United States Patent
Matsui et al.

(10) Patent No.: US 10,436,755 B2
(45) Date of Patent: Oct. 8, 2019

(54) ULTRASONIC FLAW DETECTION APPARATUS AND ULTRASONIC FLAW DETECTION METHOD

(71) Applicant: JFE Steel Corporation, Tokyo (JP)

(72) Inventors: Yutaka Matsui, Tokyo (JP); Shigeto Sakashita, Tokyo (JP); Atsushi Yonemoto, Tokyo (JP)

(73) Assignee: JFE Steel Corporation, Tokyo (JP)

( * ) Notice: Subject to any disclaimer, the term of this patent is extended or adjusted under 35 U.S.C. 154(b) by 229 days.

(21) Appl. No.: 15/324,761

(22) PCT Filed: Jul. 1, 2015

(86) PCT No.: PCT/JP2015/069011
§ 371 (c)(1),
(2) Date: Jan. 9, 2017

(87) PCT Pub. No.: WO2016/006514
PCT Pub. Date: Jan. 14, 2016

(65) Prior Publication Data
US 2017/0205380 A1    Jul. 20, 2017

(30) Foreign Application Priority Data

Jul. 10, 2014    (JP) ................................ 2014-142402

(51) Int. Cl.
*G01N 29/265* (2006.01)
*B23K 31/12* (2006.01)
*G01N 29/22* (2006.01)

(52) U.S. Cl.
CPC ......... *G01N 29/265* (2013.01); *B23K 31/125* (2013.01); *G01N 29/223* (2013.01); *G01N 2291/2675* (2013.01)

(58) Field of Classification Search
CPC ............... G01N 29/265; G01N 29/223; G01N 2291/2675; B23K 31/125
See application file for complete search history.

(56) References Cited

FOREIGN PATENT DOCUMENTS

| CN | 1042778 A | 6/1990 |
|----|-----------|--------|
| CN | 2844915 A | 12/2006 |

(Continued)

OTHER PUBLICATIONS

Supplementary European Search Report dated Jan. 26, 2018, of corresponding European Application No. 15819577.6.

(Continued)

*Primary Examiner* — Justin Seo
*Assistant Examiner* — John M Royston
(74) *Attorney, Agent, or Firm* — DLA Piper LLP (US)

(57) ABSTRACT

An ultrasonic flaw detection apparatus includes: a seam detection unit that captures a thermal image of a welded seam portion of an electric resistance welded pipe; an ultrasonic flaw detection sensor head that includes an ultrasonic probe that performs ultrasonic flaw detection on the welded seam portion; a seam position calculation unit that calculates a seam position and a bead cutting position of the electric resistance welded pipe; a bead cutting band detection unit that detects a bead cutting band of the electric resistance welded pipe; a bead cutting position calculation unit that calculates a bead cutting position of the electric resistance welded pipe; a tracking movement amount calculation unit that calculates a tracking movement amount of the ultrasonic flaw detection sensor head; and a sensor head driving unit that moves the ultrasonic flaw detection sensor head to track the welded seam portion according to the tracking movement amount.

9 Claims, 12 Drawing Sheets

(56) References Cited

FOREIGN PATENT DOCUMENTS

| JP | 01-302103 | 12/1989 | | |
|----|-----------|---------|---|---|
| JP | 03-27042 | 4/1991 | | |
| JP | 10-170228 | 6/1998 | | |
| JP | 11-314114 | 11/1999 | | |
| JP | 2006234781 A | * | 9/2006 | |
| JP | 2009222408 A | * | 10/2009 | |
| WO | WO-03022508 A1 | * | 3/2003 | ........... B23K 26/032 |

OTHER PUBLICATIONS

Korean Office Action dated Dec. 11, 2017, of corresponding Korean Application No. 10-2017-7000239, along with a Concise Statement of Relevance of Office Action in English.
Japanese Office Action dated Jan. 17, 2017, of corresponding Japanese Application No. 2014-142402, along with a Concise Statement of Relevance of Office Action in English.
Office Action dated Oct. 9, 2018, of counterpart Canadian Application No. 2,954,155.
Office Action dated Aug. 28, 2018, of counterpart Chinese Application No. 201580037351.2, along with a Search Report in English.

* cited by examiner

ULTRASONIC FLAW DETECTION APPARATUS AND ULTRASONIC FLAW DETECTION METHOD

TECHNICAL FIELD

This disclosure relates to an ultrasonic flaw detection apparatus and an ultrasonic flaw detection method for performing ultrasonic flaw detection on a welded seam portion of an electric resistance welded pipe.

BACKGROUND

Electric resistance welded pipes are generally manufactured by a process of forming a steel plate into a pipe shape and connecting both width direction end portions of the steel plate by welding while pressing the width direction end portions against each other. To obtain high welding quality in such a process of manufacturing electric resistance welded pipes, an electric resistance welded pipe is made into a product by: ultrasonic flaw detection on a welded seam portion by use of an ultrasonic flaw detection apparatus and annealing (a process of tempering the welded seam portion that has approached a quenching state by welding) of the welded seam portion with a seam annealer.

When ultrasonic flaw detection is performed on a welded seam portion, normally, after weld beads are cut or after a hydraulic test, angle beam testing in which ultrasonic wave signals are caused to be obliquely incident on the welded seam portion, is performed. In angle beam testing, ultrasonic flaw detection needs to be performed with a sensor head being positioned with respect to the welded seam portion such that the ultrasonic wave signals are incident on the welded seam portion, the sensor head including an ultrasonic probe. In particular, when focused ultrasonic wave signals are used, since focal depth of the ultrasonic wave signals becomes short, positioning thereof requires accuracy.

However, since electric resistance welded pipes are subject to various forces on manufacturing lines, their welded seam portions are not necessarily positioned on a central line of the sensor head, and may be displaced in a pipe circumference direction from the central line of the sensor head. Thus, techniques have been proposed, the techniques including: a seam position detection technique using reflected ultrasonic wave signals from a defect in a welded seam portion (see Japanese Patent Application Laid-open No. 2011-227060); and a technique of detecting a seam position from a temperature distribution obtained by imaging of a welded seam portion of an electric resistance welded pipe with an infrared camera, and further correcting a seam position by use of reflected ultrasonic wave signals from minute oxides, which are present in the welded seam portion and do not influence the quality (see Japanese Patent Application Laid-open No. 2009-222408).

However, in both of the techniques described in JP '060 and JP '408, the seam positions are detected based on the reflected ultrasonic wave signals from the minute oxides present in the welded seam portions and do not influence the quality, the reflected ultrasonic wave signals being obtained by electronic or mechanical scanning near the welded seam portions of the electric resistance welded pipes with ultrasonic wave signals in the pipe circumference direction. Therefore, according to the techniques described in JP '060 and JP '408, when the minute oxides are not present in the welded seam portions, the seam positions are not detectable.

It could therefore be helpful to provide an ultrasonic flaw detection apparatus and an ultrasonic flaw detection method enabling a seam position to be accurately detected and flaw detection on a welded seam portion to be accurately performed without reliance on reflected ultrasonic wave signals from minute oxides present in the welded seam portion.

SUMMARY

We thus provide an ultrasonic flaw detection apparatus including: a seam detection unit that captures a thermal image of a welded seam portion of an electric resistance welded pipe; an ultrasonic flaw detection sensor head that is installed downstream in a pipe manufacturing direction from the seam detection unit and includes an ultrasonic probe configured to perform ultrasonic flaw detection on the welded seam portion; a seam position calculation unit that calculates a seam position and a bead cutting position of the electric resistance welded pipe by using the thermal image of the welded seam portion captured by the seam detection unit; a bead cutting band detection unit that is installed immediately before or immediately after an installation position of the ultrasonic flaw detection sensor head and that detects a bead cutting band of the electric resistance welded pipe; a bead cutting position calculation unit that calculates, based on the bead cutting band detected by the bead cutting band detection unit, a bead cutting position of the electric resistance welded pipe; a tracking movement amount calculation unit that calculates a tracking movement amount of the ultrasonic flaw detection sensor head by using the seam position and bead cutting position calculated by the seam position calculation unit and the bead cutting position calculated by the bead cutting position calculation unit; and a sensor head driving unit that moves the ultrasonic flaw detection sensor head to track the welded seam portion of the electric resistance welded pipe according to the tracking movement amount calculated by the tracking movement amount calculation unit.

In the ultrasonic flaw detection apparatus, the seam position calculation unit calculates a temperature distribution in a pipe circumference direction of the electric resistance welded pipe from the thermal image captured by the seam detection unit, and calculates, as the seam position, a middle point between pipe circumference direction positions where temperature exceeds a predetermined threshold.

The bead cutting band detection unit includes: a first light source that emits illumination light to the vicinity of the welded seam portion from an upper left side direction of the electric resistance welded pipe; a second light source that emits illumination light to the vicinity of the welded seam portion from an upper right side direction of the electric resistance welded pipe; and an image detection unit that detects images of the vicinity of the welded seam portion when the illumination light is emitted from the first and second light sources and that is interposed between the first light source and the second light source, and the bead cutting position calculation unit calculates a minimum luminance image from the image detected when the illumination light is emitted from the first light source and the image detected when the illumination light is emitted from the second light source, calculates a luminance distribution for evaluation, which is a luminance distribution obtained as a result of calculating maximum value of luminance in a predetermined evaluation range in the pipe manufacturing direction with respect to a/the pipe circumference direction of the minimum luminance image, and based on the luminance distribution for evaluation and a predetermined threshold, calculates the bead cutting position.

The bead cutting position calculation unit calculates a chart obtained as a result of calculating maximum luminance value in the pipe circumference direction with respect to the pipe manufacturing direction of the minimum luminance image, and sets a range in the pipe manufacturing direction, in which the chart exceeds a predetermined threshold, as the predetermined evaluation range.

The bead cutting position calculation unit calculates a reference luminance distribution, which is a luminance distribution obtained as a result of calculating a maximum value of luminance in the pipe manufacturing direction with respect to the pipe circumference direction in a reference luminance calculation range set in a predetermined range of the minimum luminance image, and calculates, based on a luminance distribution obtained as a result of subtracting the reference luminance distribution from the luminance distribution for evaluation, the bead cutting position.

An ultrasonic flaw detection method applied to the ultrasonic flaw detection sensor head is an ultrasonic flaw detection method that uses water as a sound coupling material.

An ultrasonic flaw detection method includes: a seam detection step of capturing a thermal image of a welded seam portion of an electric resistance welded pipe upstream in a pipe manufacturing direction of an installation position of a ultrasonic flaw detection sensor head having a ultrasonic probe for performing ultrasonic flaw detection on the welded seam portion; a seam position calculation step of calculating a seam position and a bead cutting position of the electric resistance welded pipe by using the thermal image of the welded seam portion captured in the seam detection step; a bead cutting band detection step of detecting a bead cutting band of the electric resistance welded pipe immediately before or immediately after the installation position of the ultrasonic flaw detection sensor head; a bead cutting position calculation step of calculating, based on the bead cutting band detected in the bead cutting band detection step, a bead cutting position of the electric resistance welded pipe; a tracking movement amount calculation step of calculating a tracking movement amount of the ultrasonic flaw detection sensor head by using the seam position and bead cutting position calculated in the seam position calculation step and the bead cutting position calculated in the bead cutting position calculation step; and a sensor head driving step of moving the ultrasonic flaw detection sensor head to track the welded seam portion of the electric resistance welded pipe according to the tracking movement amount calculated in the tracking movement amount calculation step.

By the ultrasonic flaw detection apparatus and the ultrasonic flaw detection method, without reliance on reflected waves from minute oxides present in a welded seam portion, a seam position is able to be detected accurately, and flaw detection on the welded seam portion is able to be performed accurately.

REFERENCE SIGNS LIST

1 ULTRASONIC FLAW DETECTION APPARATUS
2 WELDING MACHINE
3 BEAD CUTTING MACHINE
11 ULTRASONIC FLAW DETECTION SENSOR HEAD
11a MANIPULATOR DRIVING UNIT
12 SEAM COOLING UNIT
13 SEAM DETECTION UNIT
13a SEAM DETECTION UNIT HEIGHT POSITION ADJUSTING UNIT
14 SEAM TRACKING CONTROL UNIT
14a SEAM POSITION CALCULATION UNIT
14b DELAY UNIT
14c BEAD CUTTING POSITION CALCULATION UNIT
14d TRACKING MOVEMENT AMOUNT CALCULATION UNIT
14e SPEED DETECTION UNIT
15 BEAD CUTTING BAND IMAGE DETECTION UNIT
15a, 15b LIGHT SOURCE
15c IMAGE DETECTION UNIT
16 ULTRASONIC TRANSMITTING AND RECEIVING UNIT
17 EVALUATION UNIT
P ELECTRIC RESISTANCE WELDED PIPE
R ROLLER
S STEEL PLATE

DETAILED DESCRIPTION

Hereinafter, with reference to the drawings, a configuration and operation of an ultrasonic flaw detection apparatus according to an example will be described.

Configuration

First, with reference to FIGS. 1 and 2, the configuration of the ultrasonic flaw detection apparatus according to the example will be described.

Figure 1:
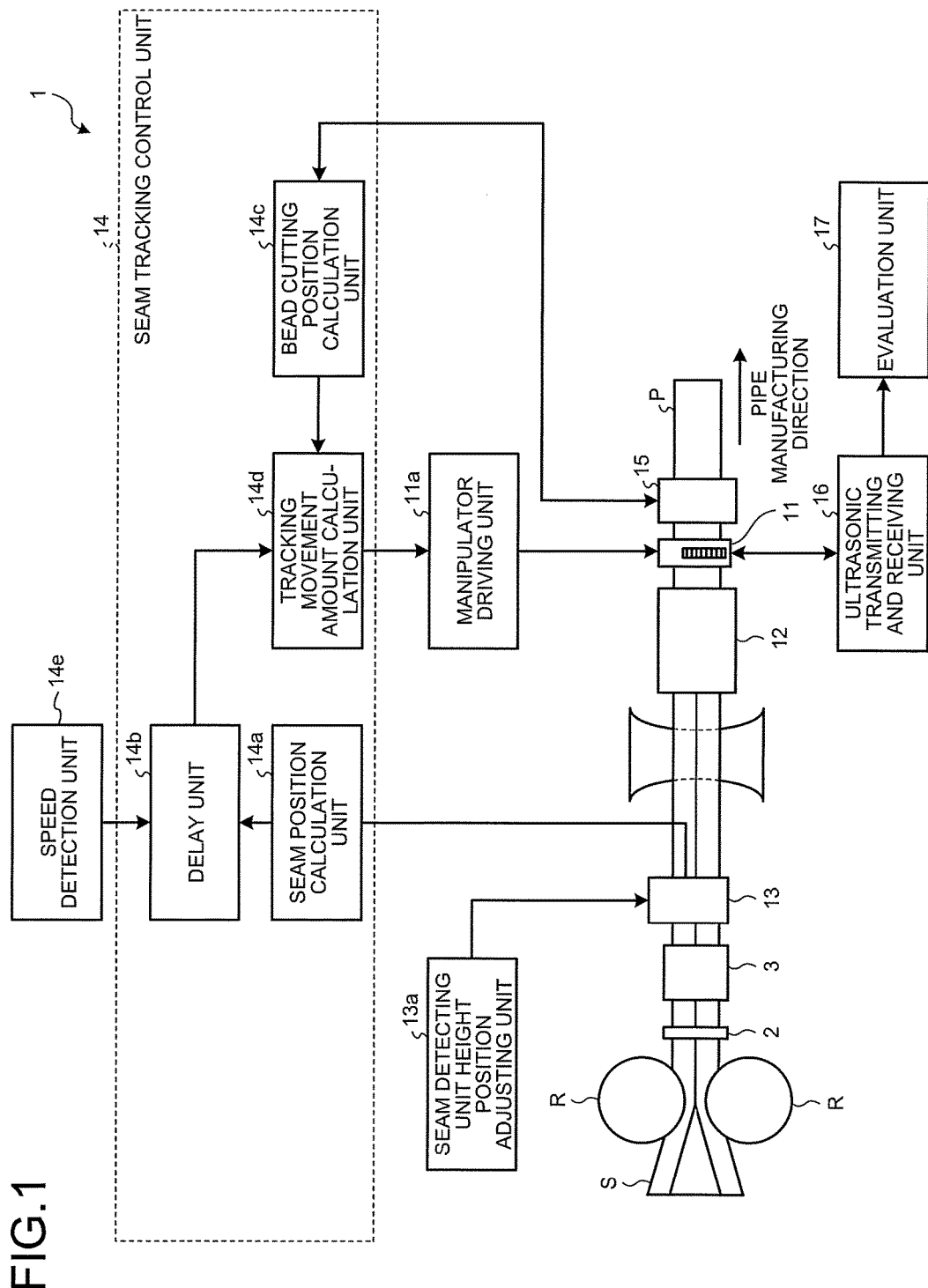
FIG. 1 is a schematic diagram illustrating an overall configuration of an ultrasonic flaw detection apparatus according to an example.

FIG. 1 is a schematic diagram illustrating an overall configuration of the ultrasonic flaw detection apparatus according to the example. FIG. 2 is a schematic diagram illustrating a configuration of a bead cutting band detection unit illustrated in FIG. 1.

As illustrated in FIG. 1, an ultrasonic flaw detection apparatus 1 according to the example is an apparatus that performs ultrasonic flaw detection on a welded seam portion of an electric resistance welded pipe P, which is manufactured by: both width direction end portions of a steel plate S being connected to each other by welding by a welding machine 2, the steel plate S having been formed into a pipe shape by rollers R; and a bead portion of a welded portion being cut by a bead cutting machine 3.

The ultrasonic flaw detection apparatus 1 includes, as main components thereof, an ultrasonic flaw detection sensor head 11, a seam cooling unit 12, a seam detection unit 13, a seam tracking control unit 14, a bead cutting band detection unit 15, an ultrasonic transmitting and receiving unit 16, and an evaluation unit 17.

The ultrasonic flaw detection sensor head 11 includes an ultrasonic probe for performing ultrasonic flaw detection on the welded seam portion of the electric resistance welded pipe P. The ultrasonic probe is configured to be able to be moved in the pipe circumference direction of the electric resistance welded pipe P by a manipulator driving unit 11a such that the ultrasonic probe tracks the welded seam portion of the electric resistance welded pipe P to enable accurate ultrasonic flaw detection on the welded seam portion, in other words, such that the welded seam portion is in a sensitivity range of the ultrasonic probe at all times.

The seam cooling unit 12 is a cooling device that is installed upstream in a pipe manufacturing direction of the ultrasonic flaw detection sensor head 11. The seam cooling unit 12 cools down the welded seam portion of the electric resistance welded pipe P such that a temperature of the welded seam portion becomes equal to or lower than about 100 degrees at an installation position of the ultrasonic flaw detection sensor head 11. The most effective method of cooling the welded seam portion is a water cooling method with a laminar nozzle, but any cooling method other than the water cooling method may be used, as long as the temperature of the welded seam portion at the installation position of the ultrasonic flaw detection sensor head 11 becomes equal to or lower than about 100 degrees.

If an ultrasonic flaw detection method applied to the ultrasonic flaw detection sensor head 11 is a water column ultrasonic method (a local immersion method) or a water film method, in which water is used as a sound coupling material, the closer the position of the ultrasonic flaw detection sensor head 11 is to the welded seam portion of the electric resistance welded pipe P, the more difficult the ultrasonic flaw detection becomes, because the water is boiled by being influenced by the heat upon the welding and transmitting and receiving of the ultrasonic wave signals are hindered. Further, the ultrasonic flaw detection sensor head 11 may be damaged by the heat. Therefore, in this example, the seam cooling unit 12 cools down the welded seam portion of the electric resistance welded pipe P upstream in the pipe manufacturing direction of the ultrasonic flaw detection sensor head 11 such that the temperature of the welded seam portion becomes equal to or lower than about 100 degrees at the installation position of the ultrasonic flaw detection sensor head 11.

The seam detection unit 13 is installed upstream in the pipe manufacturing direction of the seam cooling unit 12 and detects the welded seam portion of the electric resistance welded pipe P. In this example, the seam detection unit 13 is formed of a thermal image camera, and detects the welded seam portion from a temperature distribution of the electric resistance welded pipe P by using a thermal image captured by the thermal image camera. A height position of the thermal image camera with respect to the electric resistance welded pipe P is adjusted by a seam detection unit height position adjusting unit 13a, based on data of an outer diameter of the electric resistance welded pipe P transmitted from an operation information database, such that the thermal image is able to be captured at a predetermined focus position constantly according to the outer diameter of the electric resistance welded pipe P.

To cause the ultrasonic flaw detection sensor head 11 to accurately track the welded seam portion, the seam detection unit 13 is preferably arranged at a position that is as close as possible to the ultrasonic flaw detection sensor head 11. This is because, if the ultrasonic flaw detection sensor head 11 and the seam detection unit 13 are apart from each other; due to influence such as influence of twisting of the electric resistance welded pipe P or influence that restraining force of the forming rollers and the like gradually becomes weaker and the electric resistance welded pipe P becomes easy to be rotated in the pipe circumference direction when pipe manufacturing for a bottom portion of the electric resistance welded pipe P is approached, the ultrasonic flaw detection sensor head 11 becomes unable to accurately track the welded seam portion.

However, as described above, when the water column ultrasonic method or the water film method is applied as the ultrasonic flaw detection method, there are the problems of the transmitting and receiving of the ultrasonic wave signals being hindered by the boiling of the water and the durability of the ultrasonic probe, and thus the seam cooling unit 12 needs to be installed upstream in the pipe manufacturing direction of the ultrasonic flaw detection sensor head 11. When the welded seam portion is detected from the temperature distribution by use of the thermal image camera, after the electric resistance welded pipe P is cooled down by the seam cooling unit 12, since the temperature distribution changes due to the cooling, accurate detection of the welded seam portion becomes difficult.

Therefore, in this example, in order from upstream in the pipe manufacturing direction, the seam detection unit 13, the seam cooling unit 12, and the ultrasonic flaw detection sensor head 11 need to be installed, and the installation position of the ultrasonic flaw detection sensor head 11 and the installation position of the seam detection unit 13 consequently are apart from each other. Therefore, by executing a seam tracking control process described hereinafter, even if the installation position of the ultrasonic flaw detection sensor head 11 and the installation position of the seam detection unit 13 are apart from each other and a seam position of the electric resistance welded pipe P is displaced in the pipe circumference direction, the ultrasonic flaw detection sensor head 11 is configured to be able to accurately track the welded seam portion.

Specifically, we noticed that when an image near the ultrasonic flaw detection sensor head 11 is used, a width of a bead cutting band is able to be calculated with a change of emissivity between the bead cutting band and a portion other than the bead cutting band, and based on the calculated width of the bead cutting band, the seam position is able to be calculated. We then arranged the seam detection unit 13 upstream in the pipe manufacturing direction of the seam cooling unit 12, and arranged the bead cutting band detection unit 15, which detecting the bead cutting band, immediately before or immediately after the ultrasonic flaw detection sensor head 11 arranged downstream in the pipe manufacturing direction from the seam cooling unit 12.

The seam tracking control unit 14 is formed of an information processing device such as a computer, and functions as a seam position calculation unit 14a, a delay unit 14b, a bead cutting position calculation unit 14c, and a tracking movement amount calculation unit 14d by an arithmetic processing device such as a CPU, inside the information processing device executing a computer program. Functions of these respective units will be described later.

Figure 2:
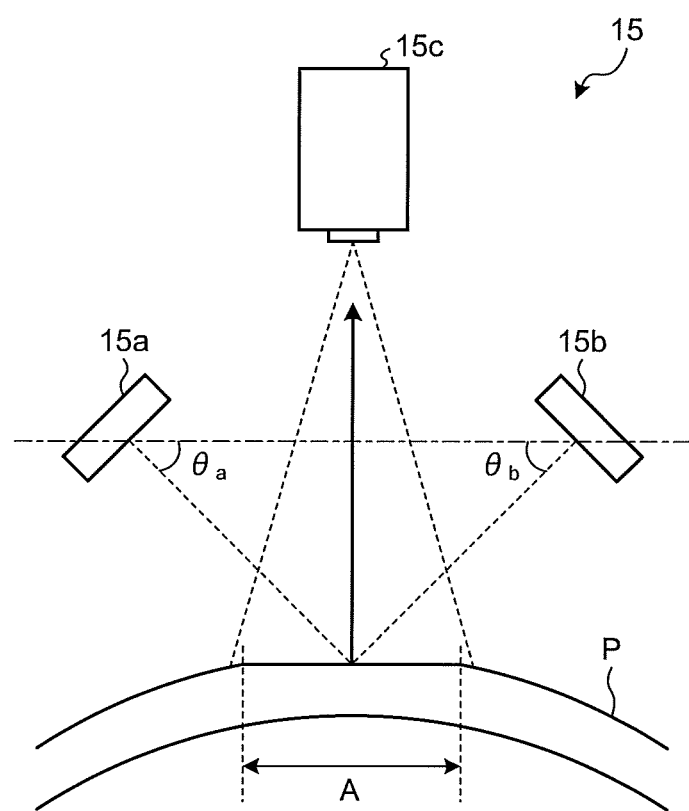
FIG. 2 is a schematic diagram illustrating a configuration of a bead cutting band detection unit illustrated in FIG. 1.

The bead cutting band detection unit 15 is a device that detects the bead cutting band of the electric resistance welded pipe P and, as illustrated in FIG. 2, includes light sources 15a and 15b, and an image detection unit 15c.

The light sources 15a and 15b are each formed of a light source such as an LED, and are installed above the welded seam portion such that incident angles of their illumination light become incident angles $\theta_a$ and $\theta_b$, respectively. The light sources 15a and 15b irradiate a peripheral surface of the electric resistance welded pipe P with illumination light, the peripheral surface including a bead cutting band A. In this example, the light sources 15a and 15b are installed above the welded seam portion such that both of incident angles of their illumination light become 45°.

The image detection unit 15c captures images of the peripheral surface of the electric resistance welded pipe P, the peripheral surface including the bead cutting band A, when the illumination light is alternately emitted from the light source 15a and the light source 15b, and outputs data of the captured images to the bead cutting position calculation unit 14c. By adopting an LED in each of the light sources 15a and 15b, images of the peripheral surface of the electric resistance welded pipe P are able to be captured while the light sources from which the illumination light is emitted are alternately switched over at high speed.

The bead cutting band detection unit 15 may detect the bead cutting band by using a thermal image camera similarly to the seam detection unit 13, or may detect the bead cutting band by using another different method such as a shape measurement method.

The ultrasonic transmitting and receiving unit 16 controls an ultrasonic flaw detection process for the electric resistance welded pipe P by outputting an instruction for transmission and receipt of ultrasonic wave signals to the ultrasonic probe that the ultrasonic flaw detection sensor head 11 includes. The ultrasonic transmitting and receiving unit 16 outputs the ultrasonic wave signals (reflected ultrasonic wave signals) reflected from the welded seam portion and received by the ultrasonic probe to the evaluation unit 17.

After performing a predetermined process with respect to the reflected ultrasonic wave signals output from the ultrasonic transmitting and receiving unit 16, the evaluation unit 17 executes, based on the reflected ultrasonic wave signals that have been subjected to the predetermined process, quality evaluation of the welded seam portion of the electric resistance welded pipe P, of whether or not a defect is present in the welded seam portion. The evaluation unit 17 provides information related to a result of the quality evaluation of the welded seam portion of the electric resistance welded pipe P to an operator by displaying and recording the result of the quality evaluation of the welded seam portion of the electric resistance welded pipe P.

In the ultrasonic flaw detection apparatus 1 having such a configuration, by executing the seam tracking control process described hereinafter, the seam tracking control unit 14 controls the ultrasonic flaw detection sensor head 11 to detect the seam position of the electric resistance welded pipe P without relying on reflected waves from minute oxides present in the welded seam portion and to track the detected seam position. Hereinafter, with reference to FIG. 3 to FIG. 8, operation of the ultrasonic flaw detection apparatus 1 when the seam tracking control process is executed will be described.

Seam Tracking Control Process

Figure 3:
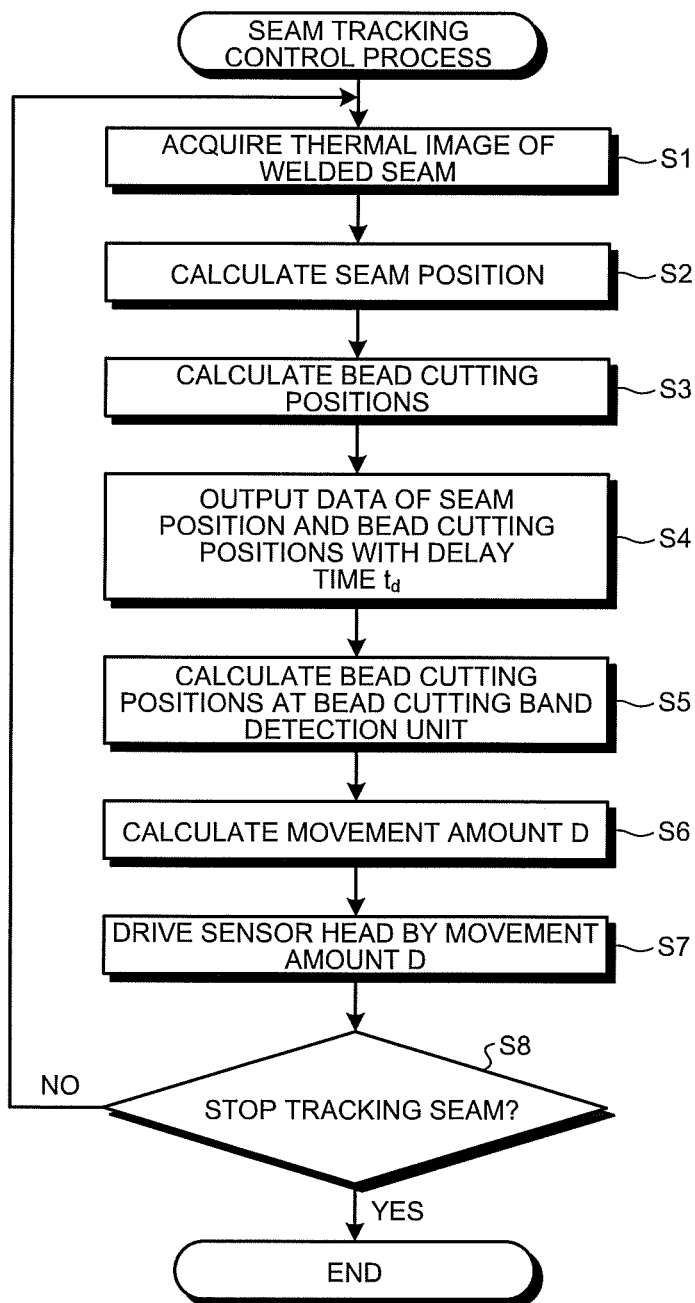
FIG. 3 is a flow chart illustrating a flow of a seam tracking control process according to the example.

FIG. 3 is a flow chart illustrating a flow of the seam tracking control process according to the example. The flow chart illustrated in FIG. 3 starts when an instruction for the ultrasonic flaw detection apparatus 1 to execute the seam tracking control process is input, and the seam tracking control process proceeds to processing of Step S1.

Figure 4:
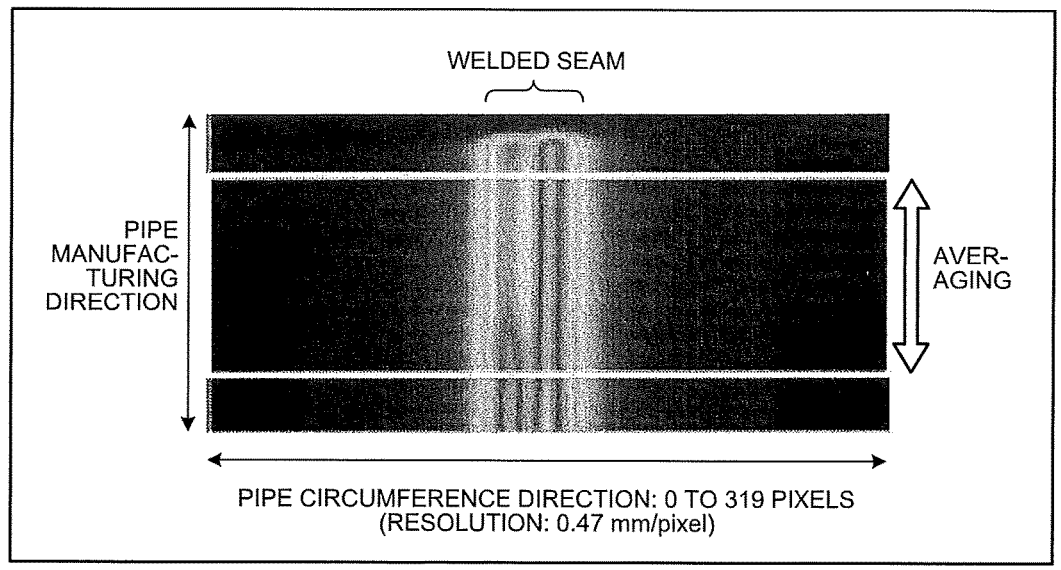
FIG. 4 is a diagram illustrating an example of a thermal image of a welded seam portion of an electric resistance welded pipe, the thermal image acquired by a seam detection unit.

In the processing of Step S1, the seam detection unit 13 acquires a thermal image of the welded seam portion of the electric resistance welded pipe P, and outputs data of the acquired thermal image to the seam tracking control unit 14. FIG. 4 is a diagram illustrating an example of the thermal image of the welded seam portion acquired by the seam detection unit 13. As illustrated in FIG. 4, the welded seam portion in a white color is able to be confirmed in a central portion of the thermal image, the white color indicating that the welded seam portion is higher in temperature than the periphery thereof. Thereby, the processing of Step S1 is completed, and the seam tracking control process proceeds to processing of Step S2.

Figure 5:
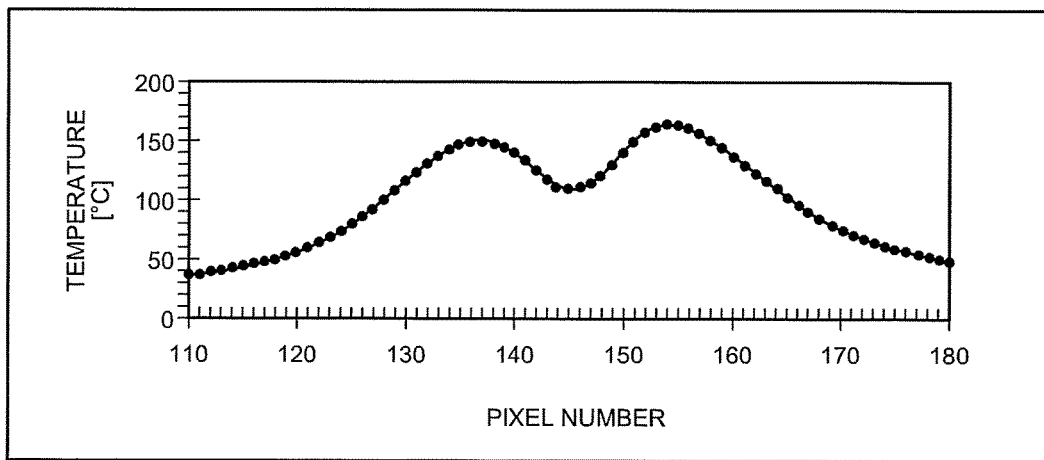
FIG. 5 is a diagram illustrating an example of a temperature distribution of the electric resistance welded pipe in a pipe circumference direction.

In the processing of Step S2, the seam position calculation unit 14a calculates a seam position Xc of the electric resistance welded pipe P by using the data of the thermal image output from the seam detection unit 13, and outputs data of the calculated seam position Xc to the delay unit 14b. Hereinafter, with reference to FIGS. 5 and 6, a method of calculating a seam position of the electric resistance welded pipe P will be described. FIG. 5 is a diagram illustrating an example of a temperature distribution of the electric resistance welded pipe P in the pipe circumference direction, and a horizontal axis and a vertical axis therein respectively represent pixel numbers in the pipe circumference direction and temperature.

Figure 6:
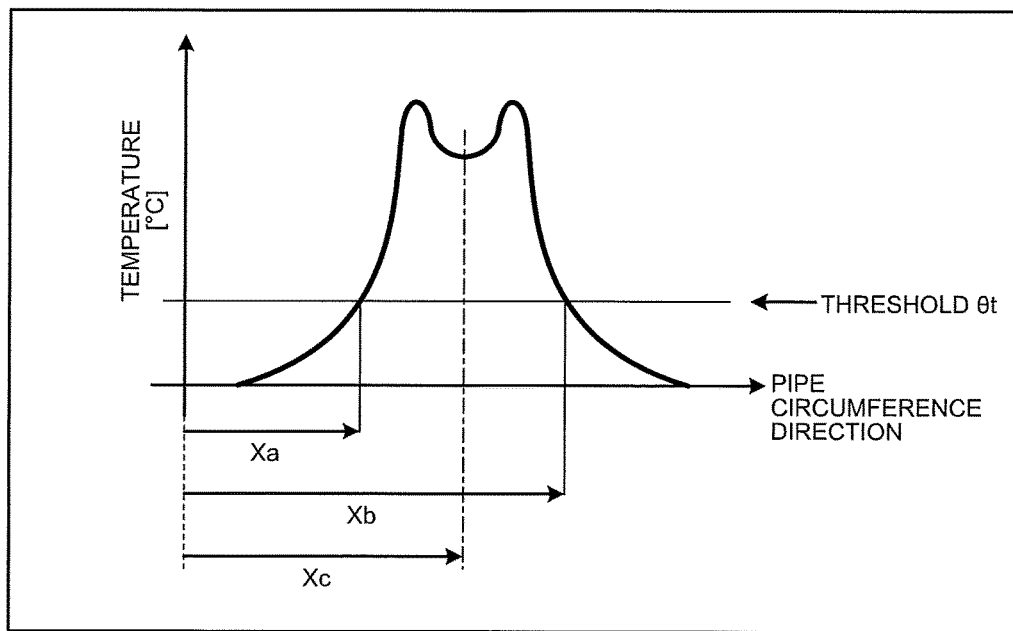
FIG. 6 is a diagram illustrating a method of calculating a seam position of the electric resistance welded pipe.

As illustrated in FIG. 5, the temperature distribution of the electric resistance welded pipe P in the pipe circumference direction has a double humped shape with a portion low in temperature near a central portion of the welded seam portion. Thus, in this example, as illustrated in FIG. 6, the seam position calculation unit 14a sets a threshold θt for the temperature distribution of the electric resistance welded pipe P in the pipe circumference direction, and calculates X-coordinates Xa and Xb, of two positions where the temperature distribution in the pipe circumference direction crosses the threshold θt. The seam position calculation unit 14a calculates the coordinate (an X-coordinate of the welded seam portion in a direction perpendicular to an axial direction of the electric resistance welded pipe P) Xc of a middle point between the X-coordinates Xa and Xb of the two positions, by using Equation (1) as the seam position Xc of the electric resistance welded pipe P at a time point when the installation position of the seam detection unit 13 is passed.

$$Xc = (Xb + Xa)/2 \qquad (1)$$

The threshold θt may be a fixed value, or may be a variable such as a value obtained as a result of multiplying a peak value of the temperature distribution in the pipe circumference direction by a predetermined fraction. Further, as a range of averaging in the temperature distribution is illustrated at a right end of FIG. 4, an average value of temperature values at plural positions of the electric resistance welded pipe P in the pipe manufacturing direction may be used as the temperature distribution of the welded seam portion in the pipe circumference direction. By using an averaged temperature value, influence of noise from the welding machine 2 or change in the thermal image due to the steam generated in the seam cooling unit 12 is able to be reduced and calculation accuracy for the seam position is able to be increased. Thereby, the processing of Step S2 is completed, and the seam tracking control process proceeds to processing of Step S3.

In the processing of Step S3, the seam position calculation unit 14a calculates bead cutting positions (pipe circumference direction end portion positions of the bead cutting band) $X_{m1}$ and $X_{m2}$ of the electric resistance welded pipe P by using the data of the thermal image output from the seam detection unit 13, and outputs data of the calculated bead cutting positions $X_{m1}$ and $X_{m2}$ to the delay unit 14b. In the temperature distribution of the electric resistance welded pipe P in the pipe circumference direction, the temperature is reduced near the central portion of the welded seam portion. Further, since the bead cutting band is more in a mirror state than the periphery thereof, the bead cutting band has emissivity of infrared rays different from the periphery. Therefore, when the temperature distribution of the welded seam portion is calculated from the thermal image using infrared rays, as illustrated in FIG. 5, a valley portion is generated in the central portion of the welded seam portion. Thus, in this example, the seam position calculation unit 14a calculates the bead cutting positions $X_{m1}$ and $X_{m2}$ by extracting a range being influenced by the emissivity due to the mirror state from the temperature distribution in the pipe circumference direction.

Figure 7:
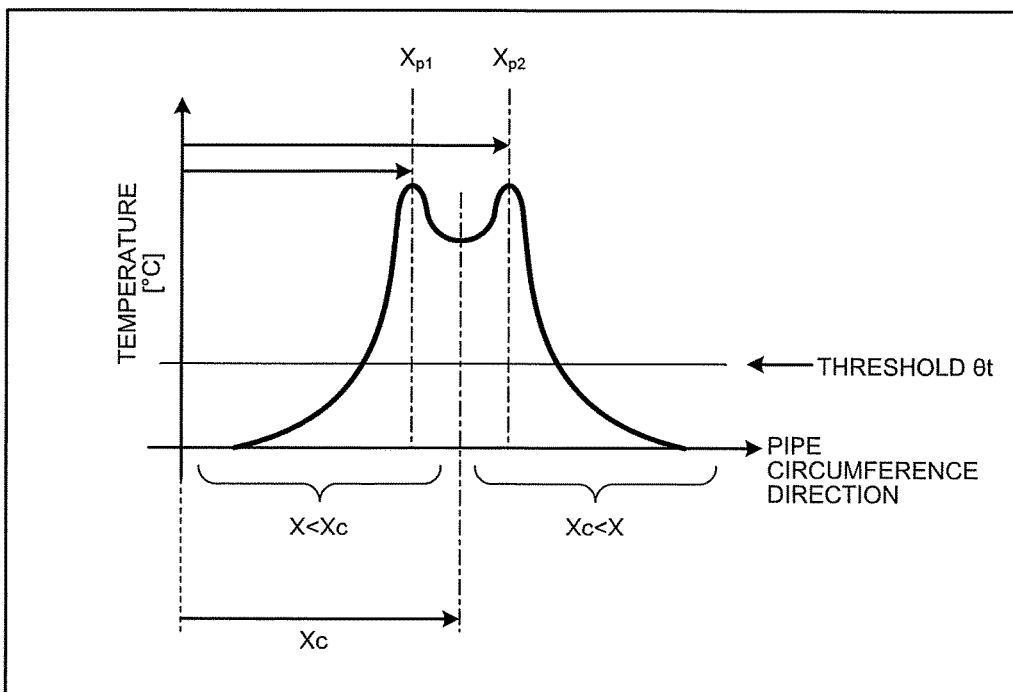
FIG. 7 is a diagram illustrating a method of calculating a bead cutting position from the temperature distribution of the electric resistance welded pipe in the pipe circumference direction.
Figure 8:
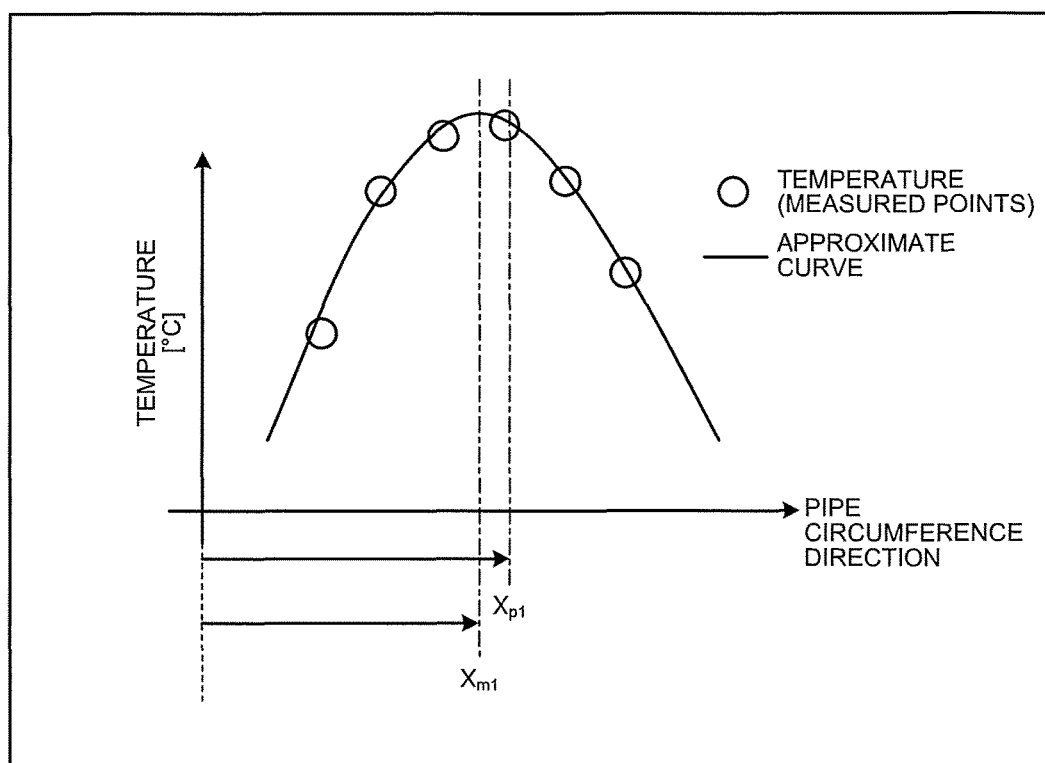
FIG. 8 is a diagram illustrating the method of calculating a bead cutting position from the temperature distribution of the electric resistance welded pipe in the pipe circumference direction.

Hereinafter, with reference to FIGS. 7 and 8, a method of calculating bead cutting positions will be described specifically. As illustrated in FIG. 7, first, the seam position calculation unit 14a calculates a pipe circumference direction position $X_{p1}$, at which the temperature becomes maximum in a range where the pipe circumference direction position X of the electric resistance welded pipe P is less than the seam position Xc, by using the seam position Xc that has been calculated in the processing of Step S2.

Next, the seam position calculation unit 14a calculates the bead cutting position $X_{m1}$, which is a pipe circumference direction position where the temperature becomes maximum, by performing curve fitting in a range of a few points before and after the pipe circumference direction position $X_{p1}$. For example, as illustrated in FIG. 8, the seam position calculation unit 14a extracts temperatures at five points before and after the pipe circumference direction position $X_{p1}$, finds an approximate curve of a quadratic function that is able to be fitted to the extracted temperatures at the five points therearound by using the least squares method, and calculates the bead cutting position $X_{m1}$, which is the pipe circumference direction position where the temperature represented by this approximate curve becomes maximum. Further, by a similar sequence for a range where the pipe circumference direction position X is greater than the seam position Xc also: the seam position calculation unit 14a calculates a pipe circumference direction position $X_{p2}$ where the temperature becomes maximum; and next calculates the bead cutting position $X_{m2}$, which is a true pipe circumference direction position where the temperature becomes maximum, by using a few points before and after the pipe circumference direction position $X_{p2}$. Thereby, the processing of Step S3 is completed, and the seam tracking control process proceeds to processing of Step S4.

In the processing of Step S4, the delay unit 14b calculates a time $t_d$ required up to when the seam position Xc and the bead cutting positions $X_{m1}$ and $X_{m2}$ pass the installation position of the bead cutting band detection unit 15, by using a pipe manufacturing speed measured by a speed detection unit 14e or the like. The delay unit 14b outputs data of the seam position Xc and bead cutting positions $X_{m1}$ and $X_{m2}$ to the tracking movement amount calculation unit 14d with a delay worth the time $t_d$. Thereby, the processing of Step S4 is completed, and the seam tracking control process proceeds to processing of Step S5.

In the processing of Step S5, the bead cutting position calculation unit 14c calculates bead cutting positions $X_{s1}$ and $X_{s2}$ at the installation position of the bead cutting band detection unit 15 and outputs data of the calculated bead cutting positions to the tracking movement amount calculation unit 14d. Details of the method of calculating the bead cutting positions $X_{s1}$ and $X_{s2}$ will be described later. Thereby, the processing of Step S5 is completed and the seam tracking control process proceeds to processing of Step S6.

In the processing of Step S6, the tracking movement amount calculation unit 14d calculates a tracking movement amount D of the ultrasonic flaw detection sensor head 11. Specifically, the tracking movement amount calculation unit 14d calculates the tracking movement amount D of the ultrasonic flaw detection sensor head 11 by using Equations (2) to (4) below. That is, first, the tracking movement amount calculation unit 14d calculates a displacement amount d between a bead cutting width central position $(X_{m1}+X_{m2})/2$ and the seam position Xc at the installation position of the seam detection unit 13 by using Equation (2).

Next, the tracking movement amount calculation unit 14d calculates a seam position $X_{pos}$, which is a coordinate obtained as a result of a bead cutting band central position $(X_{s1}+X_{s2})/2$ being corrected with the displacement amount d at the installation position of the bead cutting band detection unit 15 by Equation (3). Lastly, the tracking movement amount calculation unit 14d calculates the tracking movement amount D of the ultrasonic flaw detection sensor head 11, which is a difference between the seam position $X_{pos}$ and a target value $X_d$ that has been set in advance, by Equation (4). Thereby, the processing of Step S6 is completed, and the seam tracking control process proceeds to processing of Step S7.

$$d = Xc - \left(\frac{X_{m1} + X_{m2}}{2}\right) \tag{2}$$

$$X_{pos} = \left(\frac{X_{s1} + X_{s2}}{2}\right) + d \tag{3}$$

$$D = X_{pos} - X_d \tag{4}$$

In the processing of Step S7, the seam tracking control unit 14 controls the manipulator driving unit 11a to move the ultrasonic flaw detection sensor head 11 by the tracking movement amount D calculated in the processing of Step S6. Thereby, the processing of Step S7 is completed and the seam tracking control process proceeds to processing of Step S8.

In the processing of Step S8, the ultrasonic flaw detection apparatus 1 determines whether or not there has been an instruction to stop the seam tracking control process. If, as a result of the determination, there has been no instruction to stop the seam tracking control process, the ultrasonic flaw detection apparatus 1 returns the seam tracking control process to the processing of Step S1. On the contrary, if there has been an instruction to stop the seam tracking control process, the ultrasonic flaw detection apparatus 1 ends the seam tracking control process.

Bead Cutting Position Calculation Process

Next, with reference to FIG. 9 to FIG. 14, the above mentioned bead cutting position calculation process of Step S5 will be described.

Figure 9:
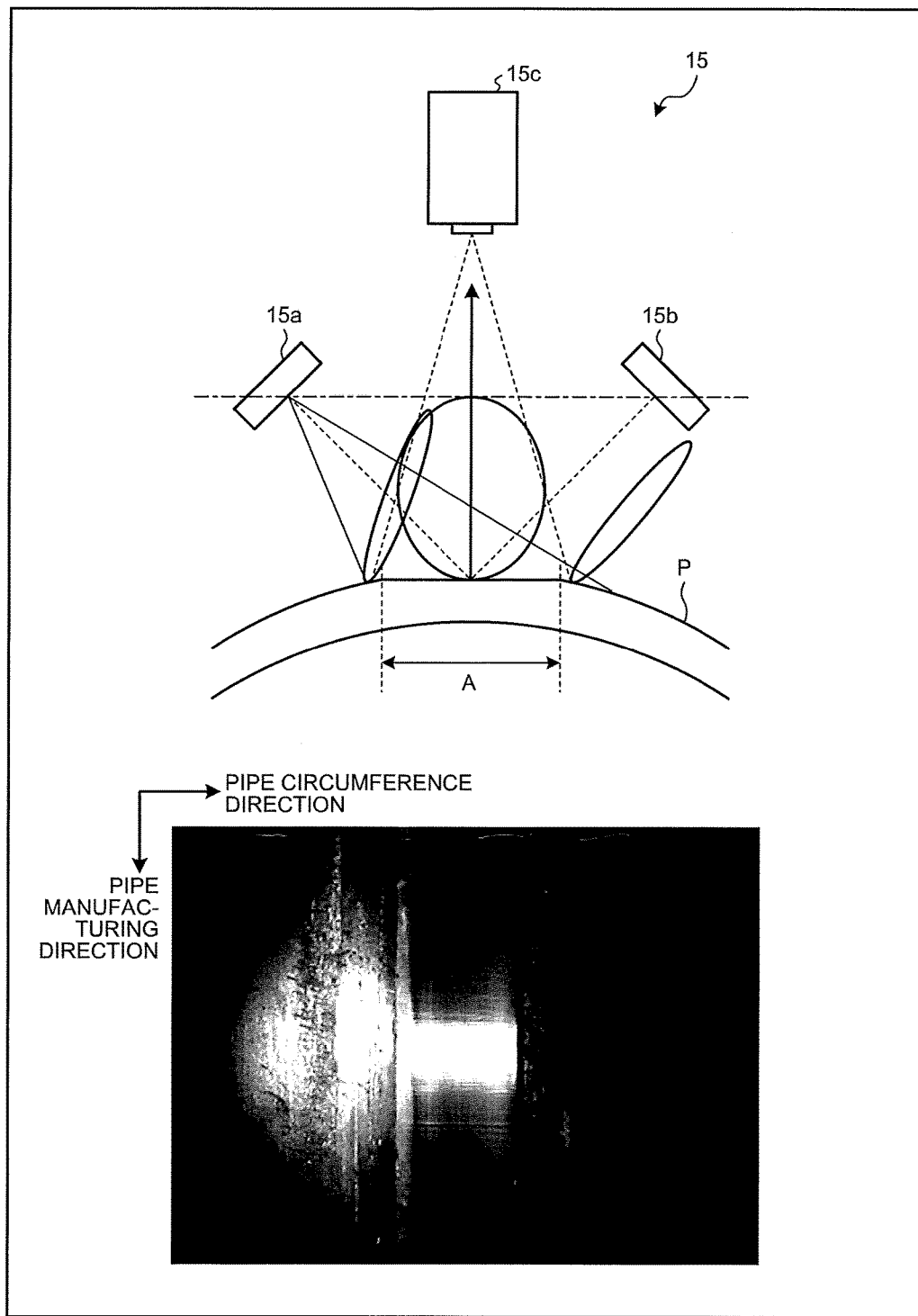
FIG. 9 is a diagram illustrating an example of an image of a bead cutting band captured by irradiation with illumination light from one of light sources.
Figure 10:
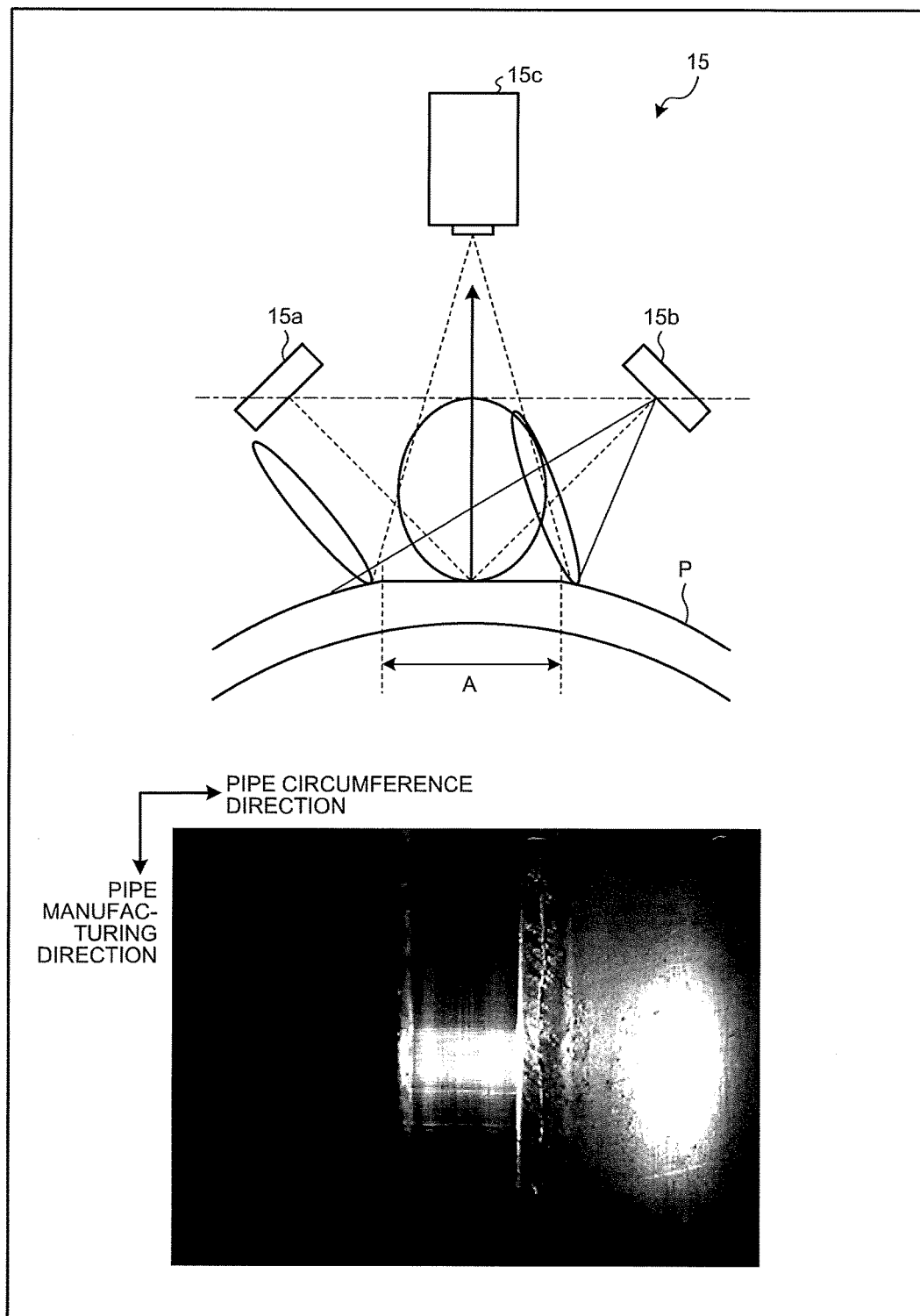
FIG. 10 is a diagram illustrating an example of an image of the bead cutting band captured by irradiation with illumination light from the other light source.

FIGS. 9 and 10 are diagrams illustrating examples of images of the bead cutting band captured by irradiation with illumination light from the light sources 15a and 15b, respectively. The images illustrated in FIGS. 9 and 10 are images acquired by imaging the same bead cutting band.

Generally, bead cutting bands have metallic luster and fine lines extending in the pipe manufacturing direction of the electric resistance welded pipes are continuously formed in bead cutting bands. Therefore, as illustrated in FIGS. 9 and 10, reflected light is generated in the bead cutting band, the reflected light having high diffusibility with respect to the illumination from the pipe circumference direction of the electric resistance welded pipe. In contrast, unlike the bead cutting band, a base surface portion of the electric resistance welded pipe has neither specularity nor fine lines. Therefore, on the base surface portion of the electric resistance welded pipe, the amount of reflected light drastically decreases as the displacement from a specular reflection position is increased.

Therefore, by performing a minimum luminance calculation process for the two images captured when the irradiation is performed with the separate left and right illumination light, that is, with the illumination light from the light source 15a and the light source 15b, only a high luminance portion high in both reflectivity and diffusibility is able to be extracted as the bead cutting band. Hereinafter, with reference to FIG. 11, a method of extracting the bead cutting band by the minimum luminance calculation process will be described.

Figure 11:
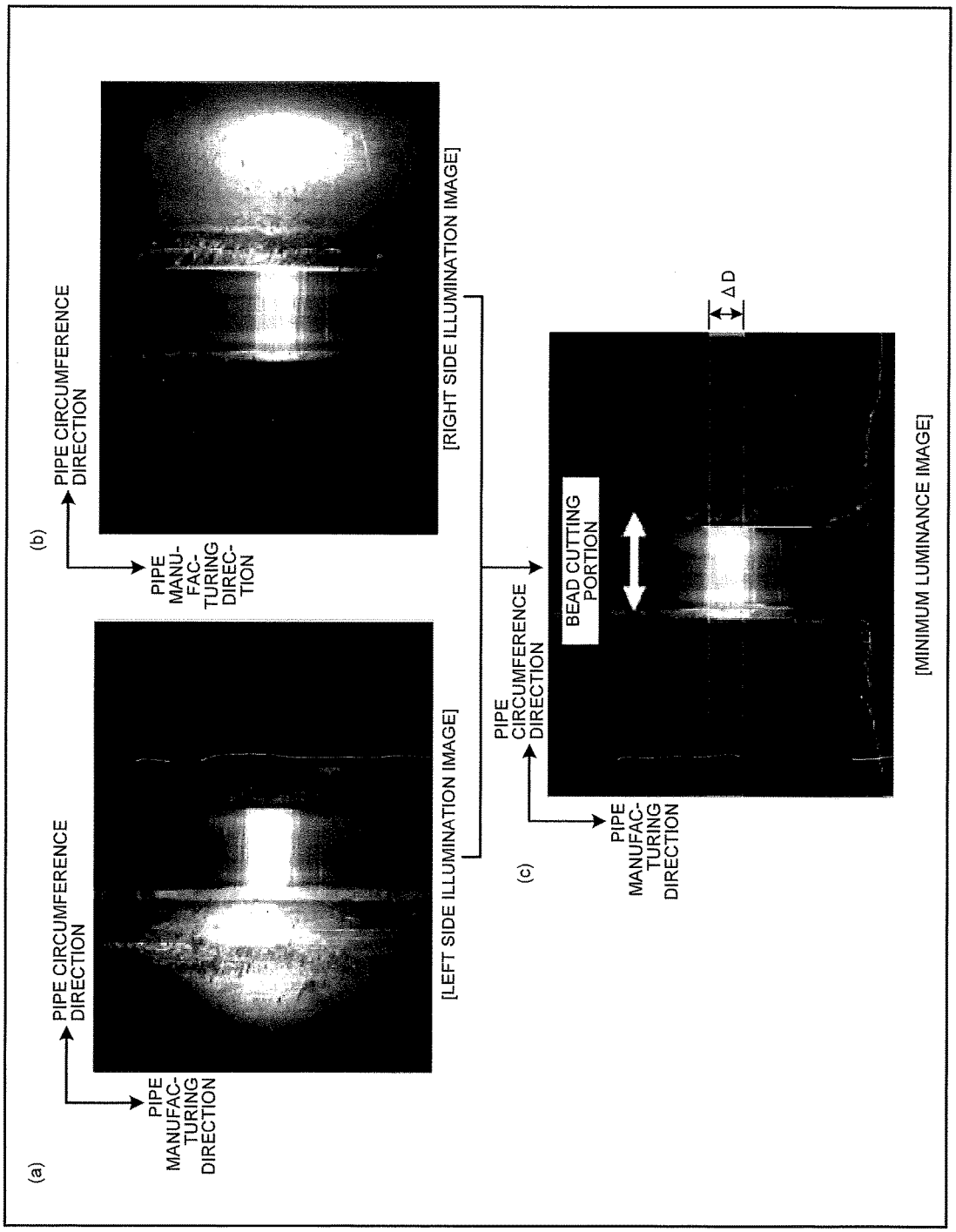
FIGS. 11(a)-(c) are diagrams illustrating a method of extracting the bead cutting band by a minimum luminance calculation process.

FIG. 11 is a diagram illustrating the method of extracting the bead cutting band by the minimum luminance calculation process. As illustrated in FIG. 11, in this extraction method, for an image captured when irradiation with illumination light from the light source 15a is performed (FIG. 11(a)) and an image captured when illumination with illumination light from the light source 15b is performed (FIG. 11(b)), a minimum luminance image (FIG. 11(c)) is obtained by comparing respective luminances at their corresponding pixel positions with each other and retaining minimum values of the luminances. By executing the minimum luminance calculation process, diffused reflected light from positions other than the bead cutting band is offset and only the image of the bead cutting band is able to be extracted.

Figure 12:
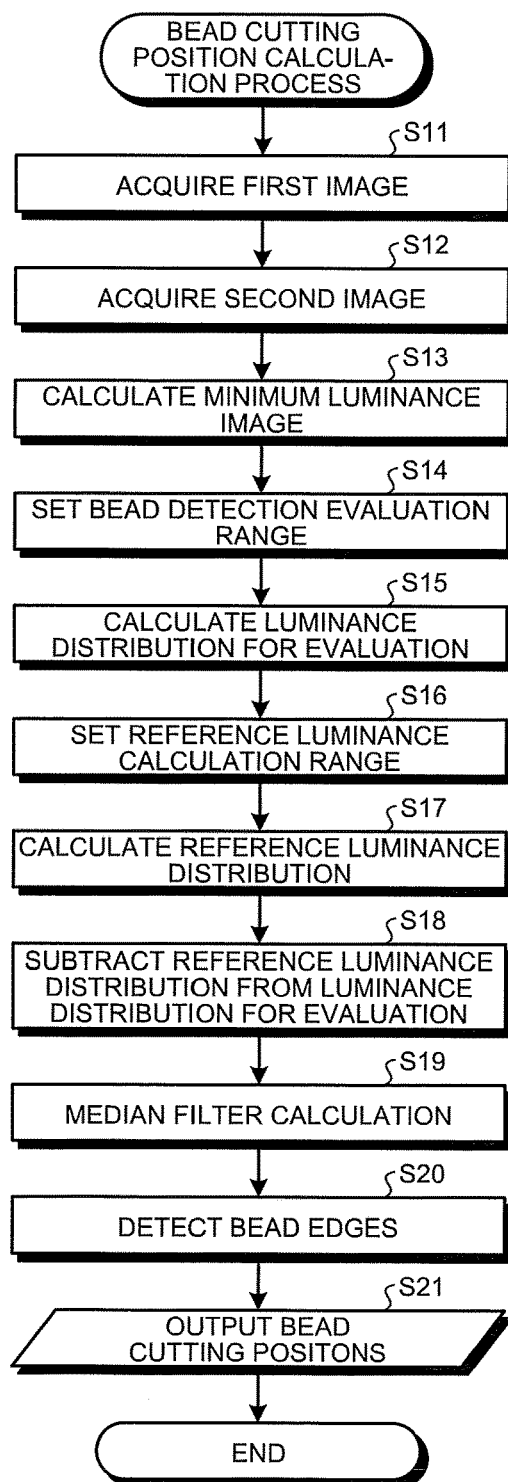
FIG. 12 is a flow chart illustrating a flow of a bead cutting position calculation process according to the example.
Figure 13:
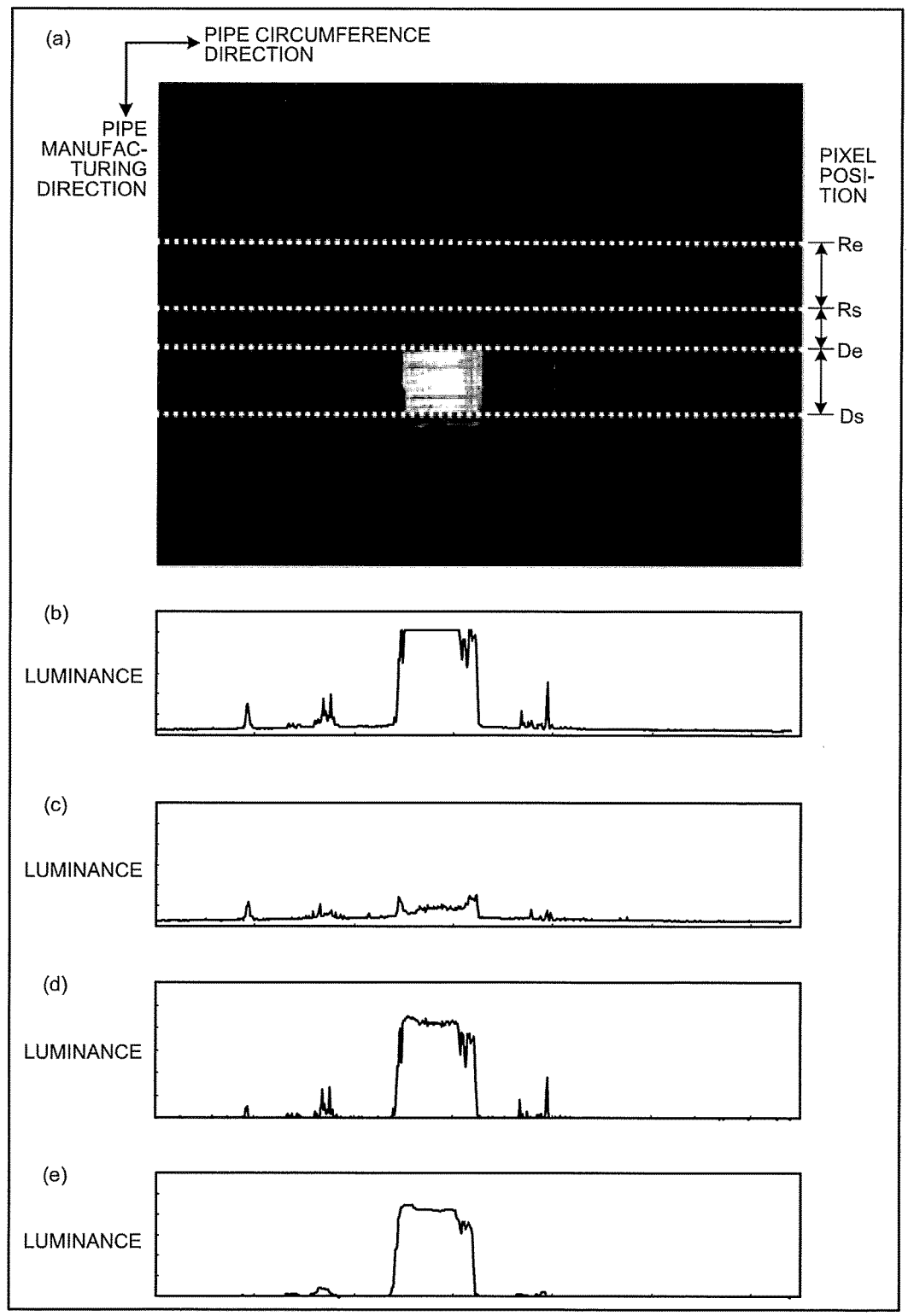
FIGS. 13(a)-(e) are diagrams illustrating processing of Steps S14 to S19 illustrated in FIG. 12.

Next, with reference to FIG. 12, a method of calculating a bead cutting position by use of the minimum luminance image will be described. FIG. 12 is a flow chart illustrating a flow of a bead cutting position calculation process according to the example. The flow chart illustrated in FIG. 12 starts when the above described processing of Step S4 is completed, and the bead cutting position calculation process proceeds to processing of Step S11.

In the processing of Step S11, the bead cutting position calculation unit 14c acquires a first image from the image detection unit 15c by controlling the light source 15a to thereby irradiate the welded seam portion with illumination light from the light source 15a. Thereby, the processing of Step S11 is completed, and the bead cutting position calculation process proceeds to processing of Step S12.

In the processing of Step S12, the bead cutting position calculation unit 14c acquires a second image from the image detection unit 15c by controlling the light source 15b to thereby irradiate the welded seam portion with illumination light from the light source 15b. Thereby, the processing of Step S12 is completed, and the bead cutting position calculation process proceeds to processing of Step S13.

In the processing of Step S13, the bead cutting position calculation unit 14c calculates a minimum luminance image by using the first image acquired by the processing of Step S11 and the second image acquired by the processing of Step S12. Thereby, the processing of Step S13 is completed, and the bead cutting position calculation process proceeds to processing of Step S14.

In the processing of Step S14, the bead cutting position calculation unit 14c sets a bead detection evaluation range in the minimum luminance image for calculating the bead cutting position. Specifically, the bead cutting position calculation unit 14c calculates a chart, which is a result of calculating the maximum luminance value in the pipe circumference direction with respect to the pipe manufacturing direction of the minimum luminance image, and sets a range in the pipe manufacturing direction where the chart exceeds a threshold, which is a range where the bead cutting band is clearly imaged, that is, the bead detection evaluation range (for example, a range between image positions De and Ds illustrated in FIG. 13(a)). Thereby, the processing of Step S14 is completed, and the bead cutting position calculation process proceeds to processing of Step S15.

In the processing of Step S15, the bead cutting position calculation unit 14c calculates a luminance distribution, which is a result of calculating the maximum value of luminance in the pipe manufacturing direction, as a luminance distribution for evaluation (see FIG. 13(b)), with respect to the pipe circumference direction in the bead detection evaluation range set in the processing of Step S14. Thereby, the processing of Step S15 is completed, and the bead cutting position calculation process proceeds to processing of Step S16.

In the processing of Step S16, the bead cutting position calculation unit 14c sets a reference luminance range (for example, a range between pixel positions Re to Rs illustrated in FIG. 13(a)) at a position that has been arbitrarily set in advance in the pipe manufacturing direction, for the bead detection evaluation range set in the processing of Step S14. Upon this setting, the bead cutting position calculation unit 14c sets the reference luminance range such that the reference luminance range and the bead detection evaluation range do not overlap each other. Specifically, the bead cutting position calculation unit 14c sets in advance a pixel distance between the reference luminance range and the bead detection evaluation range (for example, a pixel distance between the pixel position Rs and the pixel position De illustrated in FIG. 13(a)) and a pixel distance of the reference luminance range (for example, a pixel distance between the pixel position Re and the pixel position Rs illustrated in FIG. 13(a)). When the bead detection evaluation range is set by the bead cutting position calculation unit 14c through the processing of Step S14, the bead cutting position calculation unit 14c automatically sets, based on the bead detection evaluation range, the reference luminance range. The bead cutting position calculation unit 14c may display the minimum luminance image and the set bead detection evaluation range to an operator, and the operator may manually set the reference luminance range arbitrarily to not overlap the bead detection evaluation range. Thereby, the processing of Step S16 is completed and the bead cutting position calculation process proceeds to processing of Step S17.

In the processing of Step S17, the bead cutting position calculation unit 14c calculates a luminance distribution (see FIG. 13(c)), which is a result of calculating the maximum value of luminance in the pipe manufacturing direction, with respect to the pipe circumference direction in the reference luminance range set in the processing of Step S16. Thereby, the processing of Step S17 is completed, and the bead cutting position calculation process proceeds to processing of Step S18.

In the processing of Step S18, the bead cutting position calculation unit 14c calculates a luminance distribution (see FIG. 13(d)), which is a result of subtracting the reference luminance distribution calculated in the processing of Step S17 from the luminance distribution for evaluation calculated in the processing of Step S15. Thereby, the processing of Step S18 is completed, and the bead cutting position calculation process proceeds to processing of Step S19.

In the processing of Step S19, the bead cutting position calculation unit 14c performs median filter calculation with respect to the luminance distribution calculated in the processing of Step S18 (see FIG. 13(e)). In an image obtained by the minimum luminance calculation, the bead cutting band is brighter than the periphery thereof, but since the luminance level around the bead cutting band is not necessarily uniform, the bead cutting position is unable to be identified simply. Thus, in this example, the luminance distribution of a peripheral portion of the bead cutting band is corrected by the processing of Steps S15 to S19. Thereby, the processing of Step S19 is completed, and the bead cutting position calculation process proceeds to processing of Step S20.

Figure 14:
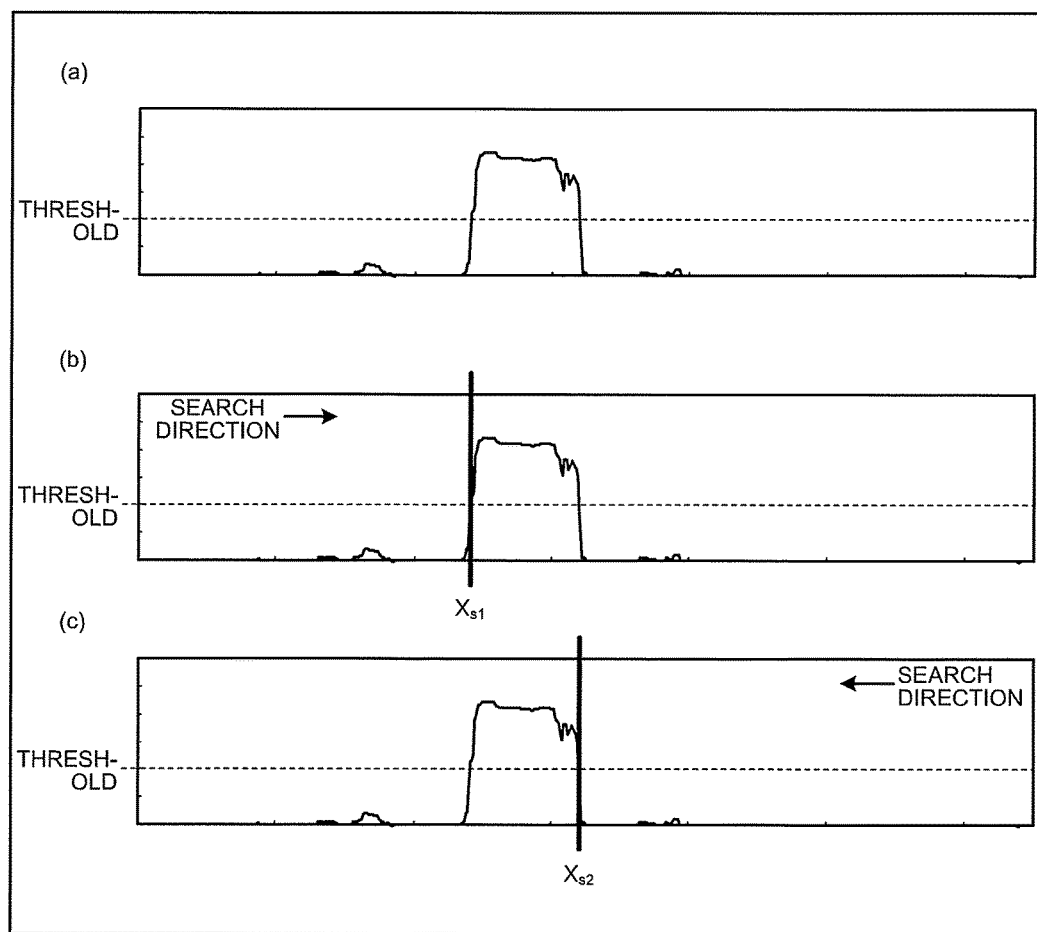
FIG. 14 is a diagram illustrating processing of Step S20 illustrated in FIG. 12.

In the processing of Step S20, the bead cutting position calculation unit 14c calculates, as illustrated in FIG. 14, positions of width direction end portions of the bead cutting band, that is, the bead cutting positions (bead edges) $X_{s1}$ and $X_{s2}$, which are positions where the corrected luminance distribution exceeds a predetermined threshold. By using a value obtained as a result of multiplying the maximum value of luminance by a predetermined fraction as the predetermined threshold used when the positions of the width direction end portions of the bead cutting band are calculated, the luminance variation in the bead cutting band is able to be dealt with. Thereby, the processing of Step S20 is completed, and the bead cutting position calculation process proceeds to processing of Step S21.

In the processing of Step S21, the bead cutting position calculation unit 14c outputs data of the bead cutting positions $X_{s1}$ and $X_{s2}$ calculated in the processing of Step S20, to the tracking movement amount calculation unit 14d. Thereby, the processing of Step S21 is completed, and the bead cutting position calculation process ends.

Thus, the ultrasonic flaw detection apparatus 1 according to the example includes: the seam detection unit 13 that captures a thermal image of a welded seam portion of the electric resistance welded pipe P; the ultrasonic flaw detection sensor head 11, which is installed downstream in the pipe manufacturing direction from the seam detection unit 13, and which has the ultrasonic probe for performing ultrasonic flaw detection on the welded seam portion; the seam position calculation unit 14a that calculates a seam position and a bead cutting position of the electric resistance welded pipe P by using the thermal image of the welded seam portion captured by the seam detection unit 13; the bead cutting band detection unit 15 installed immediately before or immediately after the installation position of the ultrasonic flaw detection sensor head 11, and detects a bead cutting band of the electric resistance welded pipe P; the bead cutting position calculation unit 14c that calculates, based on the bead cutting band detected by the bead cutting band detection unit 15, a bead cutting position of the electric resistance welded pipe P; the tracking movement amount calculation unit 14d that calculates a tracking movement amount of the ultrasonic flaw detection sensor head 11 by using the seam position and the bead cutting position calculated by the seam position calculation unit 14a and the bead cutting position calculated by the bead cutting position calculation unit 14c; and the manipulator driving unit 11a that moves the ultrasonic flaw detection sensor head 11 to track the welded seam portion of the electric resistance welded pipe P according to the tracking movement amount calculated by the tracking movement amount calculation unit 14d. Thereby, without reliance on reflected waves from minute oxides present in a welded seam portion, a seam position is able to be detected accurately, and flaw detection on the welded seam portion is able to be performed accurately.

The example has been described above, but this disclosure is not limited by the description and drawings forming a part of the disclosure. That is, any other examples, operation techniques, and the like implemented by those skilled in the art or the like based on the example are all included in the scope of this disclosure.

INDUSTRIAL APPLICABILITY

An ultrasonic flaw detection apparatus and an ultrasonic flaw detection method are provided that enable a seam position to be accurately detected and flaw detection on a welded seam portion to be accurately performed without reliance on reflected ultrasonic wave signals from minute oxides present in the welded seam portion.

The invention claimed is:

1. An ultrasonic flaw detection apparatus, comprising:
   a seam detection unit that captures a thermal image of a welded seam portion of an electric resistance welded pipe;
   an ultrasonic flaw detection sensor head installed downstream in a pipe manufacturing direction from the seam detection unit and includes an ultrasonic probe configured to perform ultrasonic flaw detection on the welded seam portion;
   a seam position calculation unit that calculates a seam position and a bead cutting position of the electric resistance welded pipe by using the thermal image of the welded seam portion captured by the seam detection unit;
   a bead cutting band detection unit installed spatially immediately before or immediately after an installation position of the ultrasonic flaw detection sensor head and detects a bead cutting band of the electric resistance welded pipe;
   a bead cutting position calculation unit that calculates, based on the bead cutting band detected by the bead cutting band detection unit, a bead cutting position of the electric resistance welded pipe;
   a tracking movement amount calculation unit that calculates a tracking movement amount of the ultrasonic flaw detection sensor head by using the seam position and bead cutting position calculated by the seam position calculation unit and the bead cutting position calculated by the bead cutting position calculation unit; and
   a sensor head driving unit that moves the ultrasonic flaw detection sensor head to track the welded seam portion of the electric resistance welded pipe according to the tracking movement amount calculated by the tracking movement amount calculation unit, wherein the bead cutting band detection unit includes: a first source that emits illumination light to a vicinity of the welded seam portion from an upper left side direction of the electric resistance welded pipe; a second light source that emits illumination light to a vicinity of the welded seam portion from an upper right side direction of the electric resistance welded pipe; and an image detection unit that detects images of the vicinity of the welded seam portion when the illumination light is emitted from the first and second light sources and interposed between the first light source and the second light source, and the bead cutting position calculation unit calculates a minimum luminance image from the image detected when the illumination light is emitted from the first light source and the image detected when the illumination light is emitted from the second light source, calculates a luminance distribution for evaluation, which is a luminance distribution obtained as a result of calculating maximum value of luminance in a predetermined evaluation range in the pipe manufacturing direction with respect to a/the pipe circumference direction of the minimum luminance image, and based on the luminance distribution for evaluation and a predetermined threshold, calculates the bead cutting position.

2. The ultrasonic flaw detection apparatus according to claim 1, wherein the seam position calculation unit calculates a temperature distribution in a pipe circumference direction of the electric resistance welded pipe from the thermal image captured by the seam detection unit and calculates, as the seam position, a middle point between pipe circumference direction positions where temperature exceeds a predetermined threshold.

3. The ultrasonic flaw detection apparatus according to claim 1, wherein the bead cutting position calculation unit calculates a chart obtained as a result of calculating maximum luminance value in the pipe circumference direction with respect to the pipe manufacturing direction of the minimum luminance image, and sets a range in the pipe manufacturing direction in which the chart exceeds a predetermined threshold, as the predetermined evaluation range.

4. The ultrasonic flaw detection apparatus according to claim 1, wherein the bead cutting position calculation unit calculates a reference luminance distribution, which is a luminance distribution obtained as a result of calculating a maximum value of luminance in the pipe manufacturing direction with respect to the pipe circumference direction in a reference luminance calculation range set in a predetermined range of the minimum luminance image and calculates, based on a luminance distribution obtained as a result of subtracting the reference luminance distribution from the luminance distribution for evaluation, the bead cutting position.

5. The ultrasonic flaw detection apparatus according to claim 1, wherein an ultrasonic flaw detection method being applied to the ultrasonic flaw detection sensor head is an ultrasonic flaw detection method that uses water as a sound coupling material.

6. The ultrasonic flaw detection apparatus according to claim 2, wherein an ultrasonic flaw detection method being applied to the ultrasonic flaw detection sensor head is an ultrasonic flaw detection method that uses water as a sound coupling material.

7. The ultrasonic flaw detection apparatus according to claim 3, wherein an ultrasonic flaw detection method being applied to the ultrasonic flaw detection sensor head is an ultrasonic flaw detection method that uses water as a sound coupling material.

8. The ultrasonic flaw detection apparatus according to claim 4, wherein an ultrasonic flaw detection method being applied to the ultrasonic flaw detection sensor head is an ultrasonic flaw detection method that uses water as a sound coupling material.

9. An ultrasonic flaw detection method comprising:

a seam detection step of capturing a thermal image of a welded seam portion of an electric resistance welded pipe upstream in a pipe manufacturing direction of an installation position of a ultrasonic flaw detection sensor head having a ultrasonic probe for performing ultrasonic flaw detection on the welded seam portion;

a seam position calculation step of calculating a seam position and a bead cutting position of the electric resistance welded pipe by using the thermal image of the welded seam portion captured in the seam detection step;

a bead cutting band detection step of detecting a bead cutting band of the electric resistance welded pipe spatially immediately before or immediately after the installation position of the ultrasonic flaw detection sensor head;

a bead cutting position calculation step of calculating, based on the head cutting band detected in the bead cutting band detection step, a bead cutting position of the electric resistance welded pipe;

a tracking movement amount calculation step of calculating a tracking movement amount of the ultrasonic flaw detection sensor head by using the seam position and bead cutting position calculated in the seam position calculation step and the bead cutting position calculated in the bead cutting position calculation step; and a sensor head driving step of moving the ultrasonic flaw detection sensor head to track the welded seam portion of the electric resistance welded pipe according to the tracking movement amount calculated in the tracking movement amount calculation step, wherein the bead cutting band detection step includes: a first light source that emits illumination light to a vicinity of the welded seam portion from an upper left side direction of the electric resistance welded pipe; a second light source that emits illumination light to a vicinity of the welded seam portion from an upper right side direction of the electric resistance welded pipe; and an image detection unit that detects images of the vicinity of the welded seam portion when the illumination light is emitted from the first and second light sources and interposed between the first light source and the second light source, and the bead cutting position calculation step calculates a minimum luminance image from the image detected when the illumination light is emitted from the first light source and the image detected when the illumination light is emitted from the second light source, calculates a luminance distribution for evaluation, which is a luminance distribution obtained as a result of calculating maximum value of luminance in a predetermined evaluation range in the pipe manufacturing direction with respect to a/the pipe circumference direction of the minimum luminance image, and based on the luminance distribution for evaluation and a predetermined threshold, calculates the bead cutting position.

\* \* \* \* \*

UNITED STATES PATENT AND TRADEMARK OFFICE
CERTIFICATE OF CORRECTION

PATENT NO. : 10,436,755 B2
APPLICATION NO. : 15/324761
DATED : October 8, 2019
INVENTOR(S) : Matsui et al.

Page 1 of 1

It is certified that error appears in the above-identified patent and that said Letters Patent is hereby corrected as shown below:

In the Claims

In Column 15
At Line 5, Claim 1 please insert --light-- after "first".

In Column 16
At Line 32, Claim 9 please change "the head cutting" to --the bead cutting--.

Signed and Sealed this
Nineteenth Day of May, 2020

Andrei Iancu
*Director of the United States Patent and Trademark Office*